G. D. ROGERS.
HIGH TENSION DISCHARGE APPARATUS.
APPLICATION FILED FEB. 3, 1920.
Reissued June 22, 1920. 14,896.
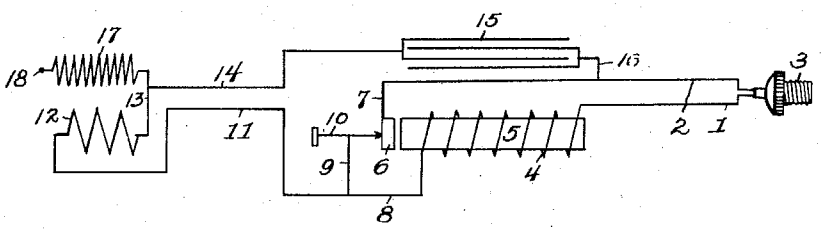
Witness
J. E. Lyles
Inventor
George D. Rogers
By Shepherd & Campbell
Attorneys

UNITED STATES PATENT OFFICE.

GEORGE D. ROGERS, OF CLEVELAND, OHIO.

HIGH-TENSION DISCHARGE APPARATUS.

14,896. Specification of Reissued Letters Patent. Reissued June 22, 1920.

Original No. 1,092,398, dated April 7, 1914, Serial No. 770,903, filed May 31, 1913. Application for reissue filed February 3, 1920. Serial No. 356,049.

*To all whom it may concern:*

Be it known that I, GEORGE D. ROGERS, a citizen of the United States, residing at Cleveland, in the county of Cuyahoga and State of Ohio, have invented certain new and useful Improvements in High-Tension Discharge Apparatus, of which the following is a specification.

This invention relates to electrical apparatus and particularly to improvements for producing high tension discharges from currents of relatively low voltage such as may be obtained from an ordinary electric light wall socket.

The invention was especially designed for use in connection with therapeutical instruments, though it will be understood that it is not intended to limit its usefulness to this purpose.

The principal object of the invention is to provide an efficient apparatus of the above character, which is simple in construction, compact in arrangement, inexpensive to manufacture, and is adapted to be connected to an ordinary electric lamp socket.

In order that the invention may be clearly understood, reference will be had to the accompanying drawing which diagrammatically illustrates the same, and the novel features thereof will be distinctly pointed out in the appended claims.

Referring to the drawing, 1 and 2 represent conductors extending from a plug 3 which is adapted to be connected to an ordinary electric lamp socket. The conductor 1 leads to an energizing coil 4 of exceeding high resistance passing around the iron core 5 of an electro-magnet, which is adapted to attract the armature 6 carried by a spring 7, connected with the conductor 2, for automatically making and breaking the circuit in the ordinary manner. The end 8 of the energizing coil 4, by means of a wire 9, is connected to the usual adjustable contact, indicated at 10, which is adapted to normally engage the armature 6 as shown. Leading from the end 8 of the energizing coil 4 is a wire 11, which extends to the primary winding 12 of a high frequency coil, of very low resistance. The other end 13 of said primary winding is connected to a wire 14, leading to a suitable condenser 15, preferably of the long flat type, which condenser is connected to the conductor 2 by means of a wire designated by 16. Said primary winding 12 of the high frequency coil preferably consists of a few turns of heavy wire, and to its end 13 is connected the secondary winding 17 comprising many turns of comparatively fine wire, in order to obtain great intensity of current. The free end or terminal 18 of the secondary winding of said high frequency coil is connected to a therapeutical instrument or other similar appliance requiring high tension charges for effective operation. By having but a single terminal as 18 leading from the secondary winding of the high frequency coil for connection to an instrument, it has been found in practice that the efficiency of the instrument has been greatly increased.

When the plug 3 is connected to an ordinary electric lamp wall socket, current of about 110 volts is drawn through the conductor 1, passes around the iron core 5 through the energizing coil 4, thence from its end 8 through the wire 9, and by the contact 10 to the armature 6, which as shown is normally in spaced relation to the end of the iron core 5. The current then passes through the spring 7 to the conductor 2, thus completing the main circuit. The iron core 5 upon being magnetized attracts the armature 6, thereby breaking the main circuit between 6 and 10. The instant the main circuit is broken, the sudden interruption of the flow of the supply current due to the breaking of the circuit, causes said current to charge the condenser 15 by passing through the wire 16, and then cease while the main circuit is broken between the armature 6 and the contact 10. Instantly, the condenser begins discharging through the wire 16 and conductor 2, through the spring 7, then across the arc between the armature 6 and the adjustable contact 10, by way of the wires 9 and 11 to energize the primary winding 12 of the high frequency coil, then back through the wires 13 and 14 to the condenser, which elements constitute the condenser discharging circuit. The moment the armature 6 is drawn to the iron core 5 and while the main circuit is still broken between the armature 6 and the adjustable contact 10, the iron core 5 becomes non-magnetic and the spring 7 returns the armature to its normal position in engagement with said contact.

As will be understood, the rapid automatic operation of the armature 6 will make and break the circuits as described, the condenser will thereby become charged and then discharge with great frequency, thus inducing currents of high tension into the primary winding 12 of the high frequency coil, and this high frequency tension is further increased by inducing said current into the fine secondary winding 17. A suitable instrument connected to the free end or terminal 18 of the secondary winding 17 would therefore receive current of very high frequency and intensity from an initial current of comparatively low voltage.

It will be understood that the invention as set forth and described is not limited to this particular arrangement of the details of construction and circuits but that the same may be modified as required in practice without departing from the spirit of the invention.

Having described my invention, what I claim is

1. In a high tension discharge apparatus the combination with a main circuit provided with means for connection to a supply current and including an induction coil and a circuit controller, of a condenser connected to the main circuit at one side of said circuit controller and a high frequency coil the primary winding of which is connected to the main circuit at the other side of the circuit controller and to the condenser, the secondary winding of said high frequency coil having one end connected to the primary winding thereof and terminating in a single end for connection to a therapeutical instrument substantially as described.

2. In a device of the character described the combination with a main circuit provided with means for connection to a supply current and including a coil, a core for the coil and a vibrating circuit controller, of a condenser connected to the main circuit at one side of said circuit controller, a high frequency coil comprising a primary and a secondary winding, a wire leading from one end of said primary winding to the main circuit at the other side of the circuit controller, and a wire leading from the other end of said primary winding to the condenser, the secondary winding of said high frequency coil having one end connected to the primary winding thereof and terminating in a single end for connection to a therapeutical instrument substantially as described.

3. In a device of the character described the combination with a main circuit provided with means for connection to a supply current and including a coil of high resistance, a core for the coil, and a vibrating circuit controller, of a condenser connected to the main circuit at one side of said circuit controller, a high frequency coil comprising a primary winding of low resistance and a secondary winding, a wire leading from one end of the primary winding to the main circuit at the other side of the circuit controller and a wire leading from the other end of said primary winding to the condenser, the secondary winding of the high frequency coil having one end connected to the primary winding thereof and terminating in a single end for connection to a therapeutical instrument substantially as described.

In testimony whereof I affix my signature.

GEO. D. ROGERS.